United States Patent [19]
Li et al.

[11] Patent Number: 5,751,869
[45] Date of Patent: May 12, 1998

[54] OPTICAL SYSTEM FOR COUPLING LIGHT FROM A SINGLE FIBER OPTIC INTO A FIBER BUNDLE

[75] Inventors: Kenneth K. Li, Arcadia; Douglas M. Brenner, Los Angeles; Chingfa Chen, West Covina, all of Calif.

[73] Assignee: Cogent Light Technologies, Inc., Santa Clarita, Calif.

[21] Appl. No.: 694,283

[22] Filed: Aug. 8, 1996

[51] Int. Cl.⁶ .................................................. G02B 6/32
[52] U.S. Cl. ............................ 385/33; 385/116; 385/119
[58] Field of Search .............................. 385/46, 33, 34, 385/35, 48, 119, 115, 116

[56] References Cited

U.S. PATENT DOCUMENTS

| | | | |
|---|---|---|---|
| 4,257,673 | 3/1981 | Matthijsse | 350/96.19 |
| 4,834,484 | 5/1989 | Gorman et al. | 350/36.18 |
| 4,863,231 | 9/1989 | Byron et al. | 350/96.16 |
| 5,016,963 | 5/1991 | Pan | 350/96.18 |
| 5,058,978 | 10/1991 | Kondoh et al. | 385/43 |
| 5,117,473 | 5/1992 | Pan | 385/33 |
| 5,377,287 | 12/1994 | Lee et al. | 385/35 |
| 5,396,571 | 3/1995 | Saadatmanesh et al. | 385/33 |

FOREIGN PATENT DOCUMENTS

| | | | |
|---|---|---|---|
| 58-156802 | 9/1983 | Japan | |
| 63-291012 | 11/1988 | Japan | 385/33 |

*Primary Examiner*—John Ngo
*Attorney, Agent, or Firm*—Rothwell, Figg, Ernst & Kurz, PC

[57] ABSTRACT

The optical coupler couples light output from the single fiber optic into the fiber optic bundle while preserving the numerical aperture of the beam output from the single fiber optic. The optical coupler also preserves any uniformity in s the beam output from the single fiber optic. The optical coupler includes a collimating device such as a magnifying lens and a diffusing device such as a hemispherical lens array. The collimating device collimates the beam output from the single fiber optic into a parallel beam having a diameter substantially equal to a diameter of the fiber optic bundle. The diffuser device diverges the collimated beam for input into the fiber optic bundle by an amount sufficient to reproduce the numerical aperture of light output from the single fiber optic. A wide variety of optical diffuser devices are disclosed, including spherical convex lens arrays, cylindrical lens arrays, pyramidal lens arrays and fresnel lenses. In one exemplary embodiment, the optical coupler is employed within a medical illumination system which transmits light from a high-intensity light source to a medical device such as a surgical headlamp, or medical endoscope or boroscope.

23 Claims, 5 Drawing Sheets

OPTICAL SYSTEM FOR COUPLING LIGHT FROM A SINGLE FIBER OPTIC INTO A FIBER BUNDLE

BACKGROUND OF THE INVENTION

1. Field of the Invention

The invention generally relates to optical systems and, in particular, to an optical system for coupling light output from one light guide into another light guide.

2. Description of Related Art

Often, it is necessary to couple light output from one optical light guide, such as a fiber optic bundle, into another optical light guide. As an example, conventional surgical headlamp illumination systems, which allow a surgeon to illuminate a small spot of light within a surgical field during an operation, typically require coupling light from a fiber optic bundle connected to a light source into a fiber optic bundle connected into the headlamp mounted to the forehead of the surgeon. The headlamp is connected to the illumination source by a pair of optical fibers, connected in sequence by a coupler, rather than by a single optical fiber, to allow the surgeon to disconnect the headlamp from the light source to facilitate freedom of movement when illumination is not needed. Also, by providing an optical coupler, a single illumination source can be used at different times with different headlamps or other medical illumination devices. Likewise, a single headlamp or other device can be used at different times with different illumination systems. Other examples of medical illumination devices which receive light along a fiber optic bundle requiring an optical coupler are endoscopes and boroscopes. Surgical headlamps, endoscopes and boroscopes, as well as other optical illumination devices, require that the beam of light received from the optical fiber bundle have a uniform intensity and numerical aperture at every position at the end surface of the fiber bundle, to thereby enable the device to uniformly illuminate a spot within a surgical field of interest. For example, within some surgical headlamps, optics are provided to allow the diameter of an illuminated spot to be varied. If the numerical aperture of light received by the surgical device is too small, it may not be possible for the internal optics to generate a sufficiently large illuminated spot. On the other hand, if the numerical aperture of input light is too large, a lot of light will be lost and the system will not be efficient.

Hence, such optical devices are designed and configured with the expectation of receiving a beam of light having uniform intensity and numerical aperture at every position at the end surface of the fiber bundle. The optical coupler which couples the fiber optic bundles, therefore, must do so in a manner which does not substantially affect either the uniformity of light output from the source or the numerical aperture thereof.

For optical systems wherein optical fiber bundles of equal diameters are coupled, the foregoing considerations are not of great concern. Adequate coupling is achieved by merely affixing the exit aperture of a first bundle with the entrance aperture of a second bundle in so-called "butt" coupling. Problems arise, however, if the first and second fiber bundles are of different diameters. Straightforward systems for coupling a smaller bundle into a larger bundle may not preserve uniform illumination and match numerical aperture. Such problems are even more acute in systems where a single fiber optic with substantially smaller diameter is coupled to a fiber optic bundle.

As an example of the latter, Cogent Light Technologies, Inc. of Santa Clarita, Calif., the Assignee of rights to the present application, provides surgical illumination devices which generate a high intensity light beam within a single fiber optic. To allow compatibility with surgical devices which use fiber optic bundles rather than a single fiber optic, an optical coupler system must be provided to couple light from the single fiber optic into the fiber optic bundles of conventional devices. Accordingly, the foregoing problems associated with preserving uniform illumination and numerical aperture arise.

One possible method for coupling a single fiber optic to a fiber optic bundle is merely to butt couple the single fiber direct to the center of the bundle. For some applications, butt coupling is acceptable even though optical fibers along the perimeter of the fiber optic bundle do not receive any input light. However, for the aforementioned system from Cogent Light Technologies, Inc., which provides a high intensity beam of light, the output intensity of the light beam from the single fiber optic is too great, and heat generated therefrom can damage the fiber optic bundle.

Another possible method for coupling light from a single fiber optic into a fiber optic bundle is to affix the fiber optic bundle a sufficient distance from an exit aperture of the single fiber optic such that an output light coming from the single fiber optic matches the input diameter of the fiber optic bundle. Depending upon the amount of power, such a configuration may avoid the problems associated with overheating portions of the fiber optic bundle while also insuring that light is transmitted into each of the individual fibers of the fiber optic bundle. However, a uniform field of illumination is not produced at the exit aperture of the fiber optic bundle. Rather, the light output from the fiber optic bundle has a diffraction pattern having alternating bright and dark regions. Such occurs because fibers at the perimeter of the bundle only receive light at an angle. As a result, the perimeter fibers transmit light into a cone having a dark central spot. The output beams from all of the various optic fibers combine to form the aforementioned diffraction pattern.

Yet another possible method for coupling a single fiber into an optical fiber bundle of larger diameter is to provide a magnifying lens between the single fiber and the bundle which collimates light output from the single fiber into a beam having a width equal to the entrance diameter of the fiber bundle. By collimating the beam, a uniform field of illumination is achieved because each of the fibers of the optical bundle receives light at substantially the same angle. However, once the beam is collimated, the original numerical aperture of the beam provided in a single fiber optic is lost. As a result, a beam output from the exit end of the fiber bundle has a small numerical aperture and any optics internal to an optical device connected to the bundle cannot properly illuminate spots of appropriate size or brightness.

Although the foregoing problems have been described with reference to a system for coupling light from a single fiber optic into a bundle, similar problems occur when coupling any two light guides of different diameters, including optical fiber bundles of different diameters.

It would be desirable to provide an improved optical system for coupling light between light guides of differing diameters, and it is to that end that certain aspects of the invention are drawn. It should be noted that the above-described proposed methods for connecting a single fiber optic into a fiber optic bundle do not necessarily represent prior art to the present invention.

SUMMARY OF THE INVENTION

In accordance with one aspect of the invention, a light guide coupling system is provided for coupling light from a first light guide into a second light guide. The optical coupler includes a collimating device for receiving and collimating light output from the first light guide, and a diffuser device, connected between the collimating device and the second light guide, for diffusing the collimated light prior to input to the second light guide. By collimating a beam output from the first light guide and then diffusing the beam, the uniformity and numerical aperture of light output from the first guide can be preserved and matched within the second light guide.

DETAILED DESCRIPTION OF THE PREFERRED EMBODIMENTS

The present invention can be utilized to couple elongate cylindrical light guides. In an exemplary embodiment, the first light guide is a single fiber optic and the second light guide is a fiber optic bundle. The single fiber optic has a diameter smaller than the diameter of the fiber optic bundle. For example, the first fiber optic light guide can have a diameter of from about 0.1 mm to about 1.0 mm. The second fiber optic light bundle typically can have a diameter of from about 2 mm to about 5 mm, although the diameter can be 6 mm, 7 mm or even larger. The collimating means can be a magnifying lens configured to collimate a cone of light output from the light-transmitting end of the single fiber optic into a beam having a diameter substantially equal to the diameter of the fiber optic bundle. The diffuser means can be an optical diffuser element configured to diffuse or diverge the collimated beam into an angle sufficient to reproduce the numerical aperture of the cone of light output from the single fiber optic. The lens diameter and the diffuser diameter usually will be about the same as that of the fiber optic light bundle.

Examples of various optical diffuser elements which can be utilized in accordance with the invention include frosted glass plates, convex lens arrays, cylindrical lens arrays, pyramidal lens arrays, and fresnel lens arrays. For the embodiments utilizing arrays of lenslets including spherical convex lenses, fresnel lenses, pyramidal lenses or cylindrical lenses, to achieve greatest uniformity in intensity and matching numerical aperture, the size of each lenslet should be as small as possible. Ideally, each lenslet should correspond to a single fiber inside the fiber bundle which is about 50 μm in diameter. In practice, a good representation of uniform intensity and matching numerical aperture can be achieved by about 100 lenslets within the aperture of the fiber bundle. For a 5 mm fiber bundle, the size of the lenslet can be as large as 500 μm. Depending on the applications, larger lenslets may also be sufficient.

Two or more optical diffuser elements may be provided. In one embodiment, the optical diffuser means are mounted within a housing which extends to the entrance aperture of the light-receiving end of the fiber optic bundle. The housing can have an internal reflecting surface to allow light diverged at sharp angles to be captured and directed into the fiber optic bundle. The housing also can extend past the magnifying lens to the exit aperture of the single fiber optic to capture light back-scattered by either the diffuser means or the magnifying lens. By providing a housing with an internal reflecting surface, the overall efficiency of the optical coupler is improved.

In accordance with one aspect of the invention, an optical coupler is provided for coupling light between optical light guides of different dimensions while preserving the uniformity and numerical aperture of light output by the first optical guide. Principles of the invention, however, can be applied to coupling light between light guides in a manner which selectively varies the uniformity or numerical aperture of the light output from the first light guide. For example, by providing a diffuser element which provides either a large or small amount of divergence to the collimated beam, the numerical aperture of the light beam transmitted into the second light guide can be set to an amount different from the numerical aperture of light output from the first light guide. Likewise, the amount of uniformity of the light beam can be varied by appropriately configuring or positioning the magnifying lens. Principles of the invention also can be applied to coupling light between optical light guides of equal diameters to vary the uniformity or numerical aperture of a light beam coupled between the two guides.

In accordance with another aspect of the invention, a surgical device such as a headlamp is provided. The surgical device receives light from a fiber optic bundle. A high intensity source of illumination is provided which feeds light into a single fiber optic. The above-described optical coupling system is employed to couple light from the single fiber optic into the fiber optic bundle while preserving uniformity of the light and the matching numerical aperture of the light.

In its various embodiments, the optical coupler of the present invention allows light to be coupled from one light guide into another while either preserving or selectively controlling the uniformity and numerical aperture of the light beam.

Referring to the figures, exemplary embodiments of the invention will be described in further detail.

Figure 1:
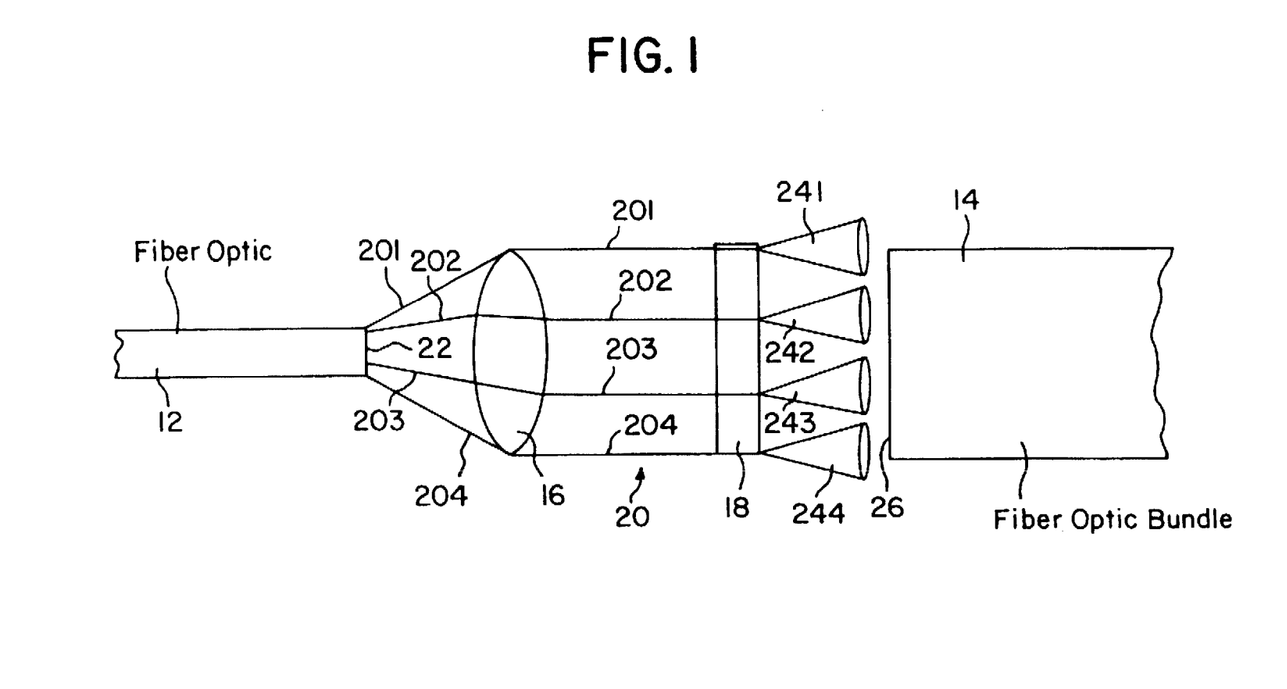
FIG. 1 is a block diagram schematically illustrating an optical coupler, configured in accordance with an exemplary embodiment of the invention, for coupling light from a single fiber optic into a fiber bundle.

FIG. 1 illustrates an optical coupler 10 mounted between a single fiber optic 12 and a fiber optic bundle 14. Optical coupler 10 includes a magnifying lens 16 and diffuser means 18. Lens 16 is sized and positioned to collimate a beam of light 20 emitted from an exit aperture 22 of fiber optic 12 into a parallel beam. Exemplary portions of beam 20 are identified by reference numerals $20_1$, $20_2$, $20_3$ and $20_4$.

As can be seen from FIG. 1, the portions of beam 20 diverge at the exit aperture 22 of fiber optic 12 by an amount defined by the numerical aperture (NA) of the fiber optic and of an illumination source (not shown in FIG. 1).

Lens 16 collimates beam 20 to orient individual beam portions $20_1$–$20_4$ in parallel, as shown. Diffuser element 18 causes each individual portion $20_1$–$20_4$ of beam 20 to diverge into respective light cones $24_1$–$24_4$. The diverged or diffused beam is then coupled into an entrance aperture 26 of optical fiber bundle 14. For clarity in illustrating the divergence of beam 20 by diffuser element 18, entrance aperture 26 is shown offset from diffuser element 18. In many applications, it is desirable to place entrance aperture 26 as close as possible to diffuser element 18 to capture as much light output from diffuser element 18 as possible.

In the embodiment illustrated in FIG. 1, lens 16 is configured to collimate beam 20 to have a beam diameter substantially equal to a diameter of optic fiber bundle 14. Diffuser element 18 is configured and positioned to diverge beam 20 to reproduce the numerical aperture of beam 20 output from fiber optic 12. In this manner, the uniformity and numerical aperture of the optical beam transmitted within fiber optic 12 is matched with fiber bundle 14. For other applications, however, it may be desirable to vary either the uniformity or the numerical aperture of the beam, and such can be accommodated by appropriately configuring or positioning lens 16 or diffuser element 18, or both. For example, to provide a smaller numerical aperture within fiber bundle 14 than within fiber optic 12, diffuser element 18 may be configured to provide a lesser amount of divergence. If less uniformity in a beam output from fiber bundle 14 is acceptable, a lens 16 of lesser optical strength can be employed which does not fully collimate beam 20. As can be appreciated, the elements of the optical system can be configured to adjust or select for these or other optical properties. For other applications, it may be desirable to select or adjust the optical characteristics of either fiber optic 12, fiber bundle 14 or both. In yet other applications, the optical coupler of the invention may be employed to couple light between fiber bundles of differing diameters.

A wide variety of optical diffuser or divergence elements can be employed in accordance with the present invention. Specific examples are illustrated in FIGS. 2–7.

Figure 2A:
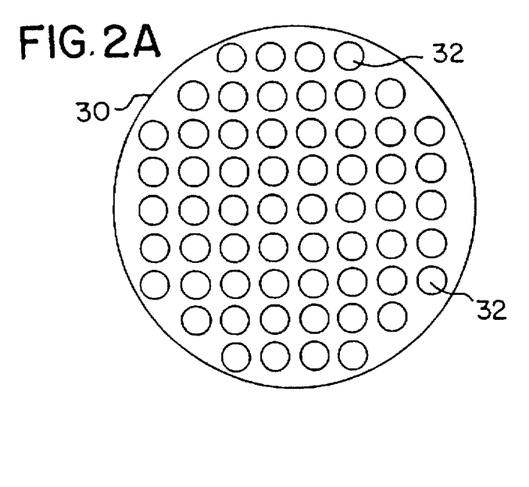
FIG. 2A is a rear view of a first exemplary embodiment of a diffuser element for use with the optical coupler of FIG. 1 wherein the diffuser element includes an array of hemispherical lenses.
Figure 2B:
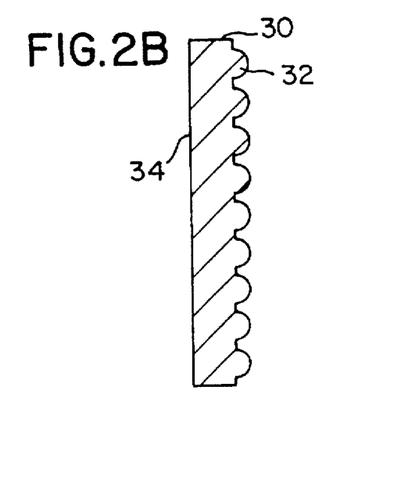
FIG. 2B is a cross-sectional view of the hemispherical lens array of FIG. 2A.

FIG. 2A illustrates a rear portion of diffuser element 30 having an array of individual spherical convex lenses 32. A side cross-sectional view of diffuser element 30 is illustrated in FIG. 2B. Each individual spherical convex lens 32 diverges light incident upon the lens into individual conical beam portions (not separately illustrated). With appropriate selection of the sizes, configurations and distribution of individual lenses 32, a desired degree of divergence can be obtained, to yield a desired numerical aperture from a parallel collimated beam transmitted therethrough.

Arrays of convex lenses having aspherical surfaces also are disclosed herein.

As shown in FIG. 2B, a front side surface 34 of diffuser element 30 may be flat. In other embodiments, the front side surface may be configured to provide additional divergence.

Figure 3A:
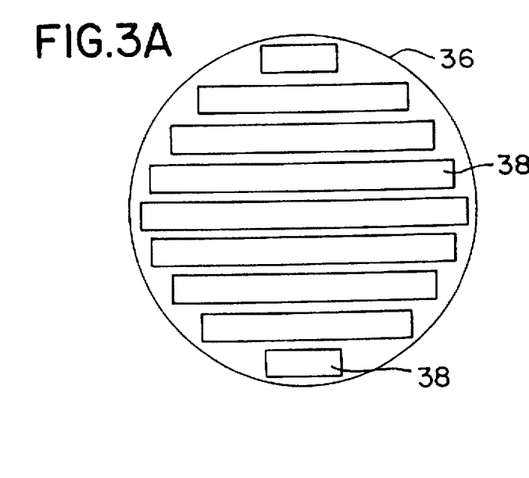
FIG. 3A is a rear view of a second exemplary embodiment of the diffuser element of FIG. 1 wherein the diffuser element includes an array of cylindrical lenses.
Figure 3B:
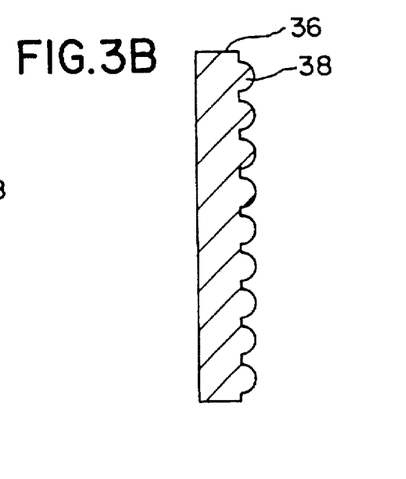
FIG. 3B is a cross-sectional view of the cylindrical lens array of FIG. 3A.

FIGS. 3A and 3B illustrate rear and cross-sectional views, respectively, of a diffuser element 36 having an array of parallel cylindrical lenses 37. Each of the cylindrical lenses operates to diverge a portion of a collimated beam about an axis extending along the cylindrical lens. Hence, divergence occurs in two dimensions, rather than in three dimensions as with the spherical convex lens array of FIGS. 2A and 2B. Nevertheless, for many applications the divergence achieved by the cylindrical array of element 36 is sufficient to achieve an adequate numerical aperture. Moreover, a cylindrical lens array is typically less expensive to fabricate than a spherical convex lens array.

Figure 4:
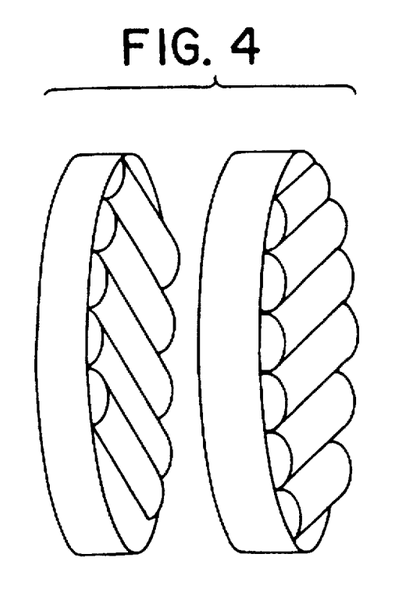
FIG. 4 is a rear perspective view of a third exemplary embodiment of the diffuser element of the optical coupler of FIG. 1 wherein a pair of cylindrical lens arrays are provided perpendicular to one another.

As illustrated in FIG. 4, a greater amount of divergence is achieved by mounting two cylindrical lens diffusers $36_1$ and $36_2$ in a perpendicular or orthogonal configuration. The combination of an orthogonally-oriented and cylindrical lens array achieves divergence similar to that of the hemispherical lens array element of FIGS. 2A and 2B while still having the advantage of being typically less expensive to manufacture.

Figure 5A:
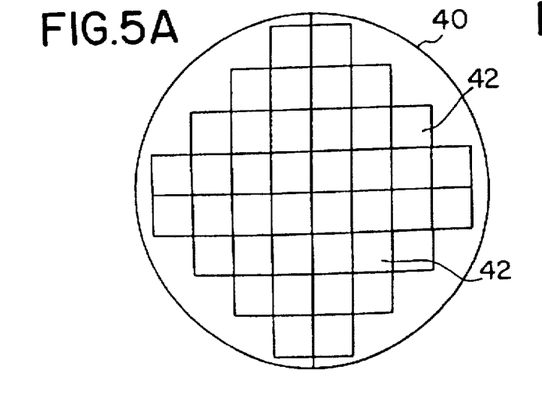
FIG. 5A is a rear view of a fourth exemplary embodiment of the diffuser element of FIG. 1 wherein an array of pyramidal lenses are provided.
Figure 5B:
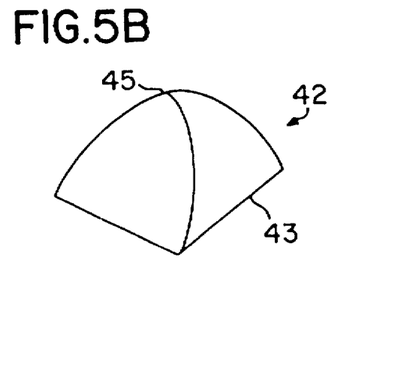
FIG. 5B is a perspective view of one of the pyramidal lenses of FIG. 5A.

FIG. 5A illustrates a diffuser element 40 which includes an array of individual pyramidal lens elements 42. An exemplary pyramidal lens 42 is illustrated in perspective view in FIG. 5B. As can be seen, pyramidal lens 42 has a substantially square base 43 and includes curved sides tapering to a vertex 45. The pyramidal array of FIG. 5A can be configured by first forming a cylindrical array as illustrated in FIG. 3A, rotating the diffuser element by 90°, then cutting a second cylindrical array orthogonal to the first.

The pyramidal array of FIG. 5A more closely approximates the hemispherical lens array of FIG. 2A than the composite cylindrical lens of FIG. 4, yet is still less expensive to fabricate than the spherical convex lens array.

Figure 6:
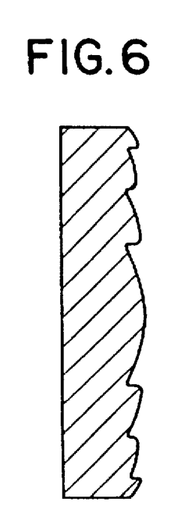
FIG. 6 is a cross-sectional view of a fifth exemplary embodiment of the diffuser element of the optical coupler of FIG. 1 wherein the diffuser element is a fresnel lens array.

FIG. 6 illustrates, in cross section, a diffuser element 44 having a fresnel lens surface 46. An array of these lenses can be used in a similar fashion as the spherical lenses shown in FIG. 2A. This is less expensive to fabricate than spherical convex lens arrays.

Figure 7:
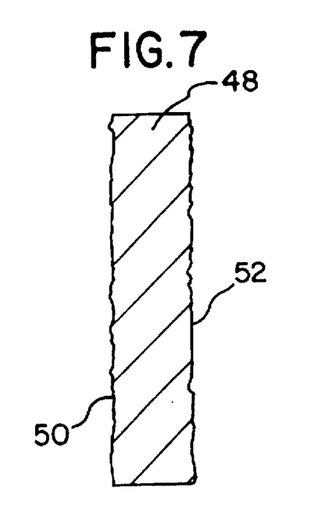
FIG. 7 is a cross-sectional view of a sixth exemplary embodiment of the diffuser element of the optical coupler of FIG. 1 wherein the diffuser element includes a frosted glass surface.

FIG. 7 illustrates another diffuser element 48 which achieves fairly uniform divergence. Diffuser element 48 includes frosted glass front and rear surfaces 50 and 52, respectively. The frosted glass diffuser element is a particularly desirable choice for an inexpensive coupler element. The frosted glass also achieves a fairly uniform divergence. However, unlike the embodiments of FIGS. 2A–6, wherein a specific amount of divergence can be achieved with an appropriate choice of optical lens components, the amount of divergence of the frosted glass element is less easily specified. Nevertheless, for many applications a frosted glass diffuser provides an acceptable amount of divergence.

Figure 8:
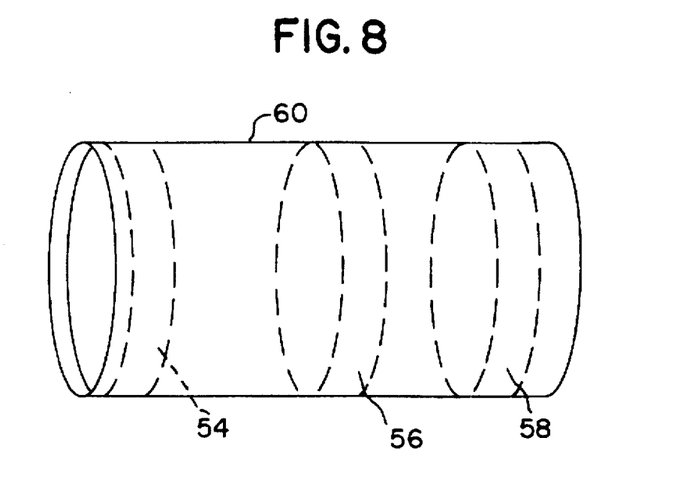
FIG. 8 is a perspective view of an alternative embodiment of the optical coupler of the invention wherein a set of diffuser elements are provided.
Figure 9:
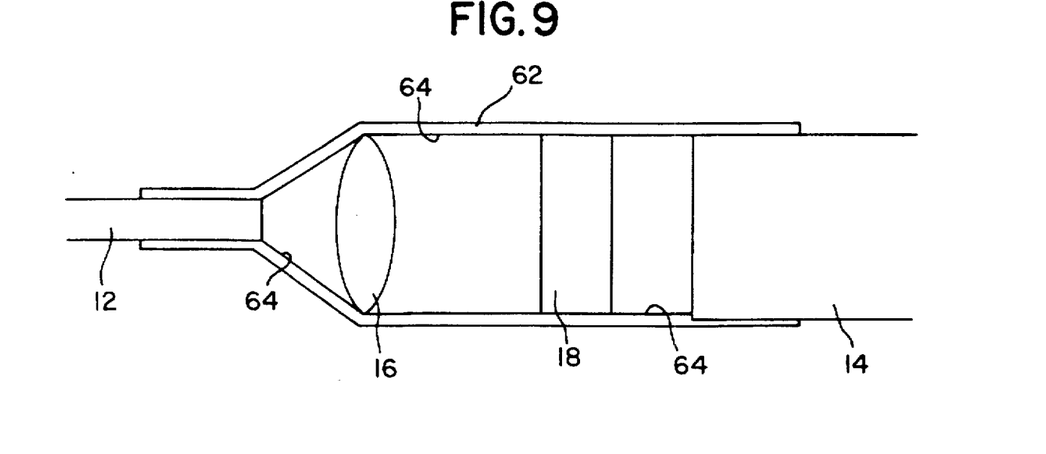
FIG. 9 is a side view of another alternative embodiment of the optical coupler of the invention wherein the optical coupler includes a housing having an internal reflecting surface.

Two or more diffuser elements may be employed in combination, as illustrated in FIG. 8. Within FIG. 8, three separate diffuser elements 54, 56 and 58 are mounted within a housing 60. The individual diffuser elements may be of the same general type or of different types. If the same general type are employed, the individual elements may nevertheless be configured to provide different amounts of divergence. The provision of several diffuser elements is desirable when a single diffuser element does not provide sufficient divergence. Such is also desirable if the amount of divergence must be controlled. The use of two or more diffuser elements in combination allows one to approximate a desired amount of divergence by matching separate diffuser elements of known divergence. For example, a set of hemispherical lens arrays may be employed wherein each array has individual hemispherical lenses of differing dimensions, thereby providing different amounts of divergence. Two or more elements from the set can be configured such that, when combined, the resulting overall amount of divergence approximates a desired amount. Within FIG. 8, the individual diffuser elements are shown spaced somewhat apart. In other implementations, the individual diffuser elements are positioned side by side or are mounted together by an adhesive. Thus, FIGS. 2A-8 illustrate various individual diffuser elements and combinations thereof for diverging collimated beam 20 of FIG. 1. Although not specifically shown in FIG. 1, optical coupler 10 is preferably mounted within a housing which allows the coupler to be easily mounted to fiber optic 12 and optic fiber bundle 14. One such housing arrangement is schematically illustrated in FIG. 9. More specifically, FIG. 9 illustrates a housing 62 which encloses optical coupler 10 and mounts to fiber optic 12 and fiber bundle 14. An interior surface 64 of housing 62 is reflective to improve the optical efficiency of the coupler by redirecting back-scattered or side-scattered light which could otherwise be lost. Depending upon the implementation, the reflective surface extends between fiber 12 and lens 16, or between lens 16 and diffuser 18, or between diffuser 18 and fiber bundle 14, or any combination thereof. A reflective coating between diffuser 18 and fiber bundle 14 helps redirect diverged light rays which might otherwise miss the entrance aperture of bundle 14. A reflective surface between optic fiber 12 and diffuser element 18 helps redirect light which is back-scattered from either lens 16 or diffuser element 18. The amount of back-scatter can further be controlled with appropriate coatings or filters provided within, between or on the various optical components.

Although not specifically shown, housing 62 preferably is configured to easily and reliably mount to optic fiber 12 and fiber bundle 14, to facilitate quick coupling of the fibers. Also preferably, housing 62 is configured to allow a variety of different-sized fibers or fiber bundles to be connected one to the other.

The ability to couple optical light guides of differing diameters while preserving the uniformity and matching numerical aperture of light beams transmitted therethrough is desirable for many applications. As can be seen, the light guide coupling system of the present invention may be configured in accordance with a wide range of embodiments.

Figure 10:
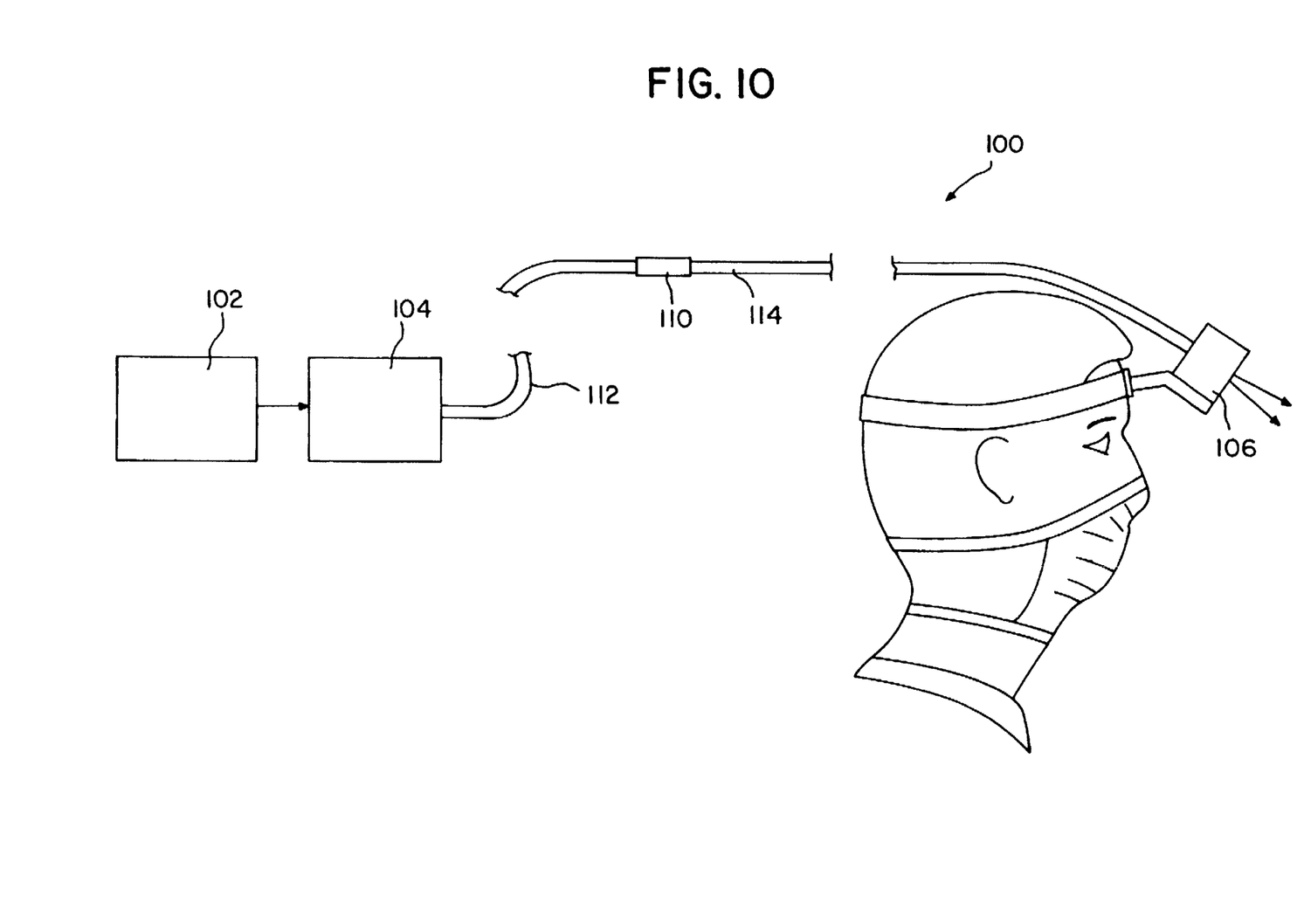
FIG. 10 is a block diagram of a medical illumination system incorporating any of the optical couplers of FIGS. 1–9.

For example, the present invention can be utilized for coupling of light into a fiber optic bundle connected to medical devices such as a surgical headlamp, or medical endoscope or boroscope. FIG. 10 illustrates a overall medical illumination system 100 incorporating any of the various embodiments of the optical coupler of FIGS. 1-9. Medical illumination system 100 of FIG. 10 includes an optical light source 102 and an off-axis optical coupler 104 for coupling light from source 102 into a fiber optic 112. Fiber optic 112 is in turn coupled to a fiber bundle 114 by an optical coupler 110. Fiber bundle 114 feeds light into medical device 106 which, in the embodiment specifically shown in FIG. 10, is a surgical headlamp. Optical light source 102 may be any of a variety of optical sources, such as a high-intensity xenon arc lamp. Likewise, optical coupler 104 may be any of a variety of conventional or non-conventional optical couplers for coupling light from source 102 into fiber optic 112. For example, coupler 104 may be an off-axis light coupler as described in U.S. Pat. No. 4,757,431, which is incorporated by reference herein. The combination of a high-intensity xenon arc lamp and an off-axis coupler allows a very high intensity beam of light to be input into fiber optic 112 for ultimate use by medical device 106.

An optical coupler in accordance with the present invention can be configured to preserve the uniformity and numerical aperture of beams transmitted within a pair of light guides. Alternatively, the uniformity, numerical aperture, or both, may be varied. Although described primarily with reference to optical fibers and fiber bundles for transmitting optical radiation, principles of the invention are applicable to the transmission of other forms of radiant energy as well. The invention is particularly applicable to systems wherein each of the light guides are circular, cylindrical light guides, but the invention is also applicable to light guides of differing configurations, including light guides having non-circular cross sections. In general, the exemplary embodiments described herein are merely provided to illustrate principles of the invention and should not be construed as limiting the scope of the invention. Rather, principles of the invention are applicable within a wide range of implementations for a wide range of applications.

We claim:

1. A light guide coupling system, comprising:
   a first optical light guide having a first diameter, the first optical light guide having a light-transmitting end;
   a collimating device for receiving and collimating light output from the light-transmitting end of the first optical light guide;
   a second optical light guide having a second diameter different from said first diameter, the second optical light guide having a light-receiving end; and
   a diffuser device positioned between the collimating device and the light-receiving end of the second light guide, for diffusing the collimated light and for directing the light into the light-receiving end of the second light guide such that the collimated light diverges into the second light guide.

2. The system of claim 1, wherein the first and second light guides are both elongate cylindrical light guides.

3. The system of claim 2, wherein the diameter of the first light guide is less than the diameter of the second light guide.

4. The system of claim 3, wherein the collimating device comprises a magnifying lens for providing a collimated beam having a diameter substantially equal to the diameter of the second light guide.

5. The system of claim 1, wherein the first light guide is a single fiber optic and the second light guide is a fiber optic bundle.

6. The system of claim 1, wherein the diffuser device is an optical diffuser element.

7. The system of claim 6, wherein the optical diffuser element comprises a glass plate having a frosted glass surface.

8. The system of claim 6, wherein the optical diffuser element comprises a lens array of convex lenses.

9. The system of claim 8, wherein the convex lenses are comprised of spherical surfaces.

10. The system of claim 8, wherein the convex lenses are comprised of aspherical surfaces.

11. The system of claim 6, wherein the optical diffuser element comprises a lens array of cylindrical lenses.

12. The system of claim 6, wherein the optical diffuser element comprises a pair of lens arrays of cylindrical lenses oriented perpendicular to one another.

13. The system of claim 6, wherein the optical diffuser element comprises a lens array of pyramidal lenses.

14. The system of claim 6, further comprising a housing mounted between the diffuser element and an entrance aperture of the light-receiving end of the second light guide, said housing having an internal reflecting surface.

15. The system of claim 6, further including a housing extending from an exit aperture of the light-transmitting first optical light guide past the collimating means to the optical diffuser element, said housing having an internal reflecting surface.

16. The system of claim 6, wherein the optical diffuser element comprises at least one fresnel lens.

17. The system of claim 1, wherein the diffuser devices comprises a plurality of individual optical diffuser elements.

18. The system of claim 17, wherein the individual optical diffuser elements are selected from the group consisting of frosted glass diffuser elements, convex lens array diffuser elements, cylindrical lens array diffuser elements, pyramidal lens array diffuser elements, and fresnel lenses.

19. The system of claim 1, wherein the diffuser device diffuses the collimated beam by an amount sufficient to produce a numerical aperture substantially equal to a numerical aperture of light output from an exit aperture of the light-transmitting end of the first optical light guide.

20. The system of claim 1, wherein the collimating device and the diffuser device include optical elements, and wherein surfaces of said optical elements include optical coatings for reducing reflections.

21. A radiant energy coupling system, comprising:

a first radiant energy guide having an output of radiant energy;

a collimating device for receiving and collimating said output from the first guide;

a second radiant energy guide having a radiant energy entrance aperture; and a diffuser device positioned between the collimating device and the entrance aperture of the second radiant energy guide, for diffusing a collimated beam received from the collimating device and for directing the beam into the entrance aperture of the second guide such that the collimated light diverges into the second light guide.

22. A surgical illumination system comprising:

a light source for radiating light;

a first optical light guide;

a first optical coupler for receiving the radiated light from the light source and for directing the radiated light into the first optical light guide;

a second optical light guide;

a second optical coupler for coupling light output from an exit aperture of the first light guide into an entrance aperture of the second light guide, said second optical coupler including:

a collimating device for receiving and collimating light output from the exit aperture of the first light guide; and a diffuser device positioned between the collimating device and the entrance aperture of the second light guide, for receiving a collimated light beam from the collimator and for diffusing and directing the collimated beam into the entrance aperture of the second light guide; and a headlamp for receiving and projecting light from an exit aperture of the second optical light guide into a surgical field.

23. In an optical system for coupling light from a first optical light guide into a second optical light guide wherein the first optical light guide has a diameter smaller than a diameter of the second optical light guide, an improvement comprising:

configuring the optical system so as to collimate a beam output from the first optical light guide into a beam having a diameter substantially equal to the diameter of the second optical light guide, and so as to diverge the collimated beam into an entrance aperture and match the numerical aperture of the second optical light guide.

\* \* \* \* \*